(12) United States Patent
Low et al.

(10) Patent No.: US 8,309,070 B2
(45) Date of Patent: Nov. 13, 2012

(54) USE OF UMBILICAL CORD BLOOD STEM CELLS TO TREAT ISCHEMIC EVENT

(75) Inventors: Walter Low, Shorewood, MN (US); Jing Xiao, Roseville, MN (US); Zhenhong Nan, Roseville, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 0 days.

(21) Appl. No.: 11/130,820

(22) Filed: May 17, 2005

(65) Prior Publication Data

US 2007/0172465 A1    Jul. 26, 2007

Related U.S. Application Data

(60) Provisional application No. 60/572,162, filed on May 17, 2004.

(51) Int. Cl.
*A01N 63/00* (2006.01)
*C12N 5/071* (2010.01)
*A01N 65/00* (2009.01)

(52) U.S. Cl. .................. 424/93.1; 424/93.7; 435/372

(58) Field of Classification Search .............. 435/325
See application file for complete search history.

(56) References Cited

U.S. PATENT DOCUMENTS

| | | | |
|---|---|---|---|
| 5,639,275 A | 6/1997 | Baetge et al. | |
| 5,843,723 A | 12/1998 | Dubensky et al. | |
| 6,245,757 B1 | 6/2001 | Chopp et al. | |
| 2002/0028510 A1* | 3/2002 | Sanberg et al. | 435/368 |
| 2002/0123141 A1 | 9/2002 | Hariri | |
| 2003/0032179 A1 | 2/2003 | Hariri | |
| 2004/0197310 A1 | 10/2004 | Sanberg et al. | |
| 2005/0169902 A1 | 8/2005 | Borlongan et al. | |
| 2005/0249708 A1* | 11/2005 | Garbuzova-Davis et al. | 424/93.7 |

FOREIGN PATENT DOCUMENTS

| | | |
|---|---|---|
| WO | WO 01/11011 | 2/2001 |
| WO | WO 02/064748 | 8/2002 |
| WO | WO 03/068937 | 8/2003 |

OTHER PUBLICATIONS

Yang, Y-G, Application of xenogeneic stem cells for induction of transplantation tolerance: Present state and future directions, Springer Semin. Immun., 26: 187-200, 2004.*
Kozlowska, H et al , Transplantation of a novel human cord blood-derived neural-like stem cell line in a rat model of cortical infarct, 2007, Stem Cells and Development, 16:481-488.*
Willing A.E. et al , 2003, Intranvenous versus intratriatal cord blood administration in a rodent model of stroke, Journal of Neuroscience Research, 73:296-307.*
van de Ven, et al, 2007, The potential of umbilical cord blood multipotent stem cells for nonhematopoietic tissue and cell regeneration, Experimental Hematology, 35:1753-1765.*
Vendrame, M et al., 2004, Infusion of human umbilical cord blood cells in a rat model of stroke,Stroke, 35:2390-2395.*
Weber, 2002, Biomaterials, 23:2003-2013.*
Abe, A., et al. "Enhanced gene transfer with fusogenic liposomes containing vesicular stomatitis virus G glycoprotein." *J. Virol.* (1998) 72:6159-6163.
Barker, J.N. et al. "Umbilical cord blood transplantation: current state of the art." *Curr Opin Oncol* (2002) 14:160-164.
Barker, J.N., et al. "Umbilical-cord blood transplantation for the treatment of cancer." (2003) *Nature Reviews* 3:526-532.
Bonadio, J., et al. "Localized, direct plasmid gene delivery in vivo: prolonged therapy results in reproducible tissue regeneration." *Nature Medicine* (1999) 5:753-759.
Bredenbeek, P.J., et al. "Sindbis virus expression vectors: packaging of RNA replicons by using defective helper RNAs." *J. Virol.* (1993) 67:6439-6446.
Broxmeyer, H.E. et al., "Human umbilical cord blood as a potential source of transplantable hematopoietic stem/progenitor cells." *PNAS*, (1989) 86(10):3828-3832.
Cai Z.H., et al., "Microencapsulated hepatocytes for bioartificial liver support." *Artif Organs.* (1988) 12(5):388-93.
Chang, P., et al., "The in vivo delivery of heterologous proteins by microencapsulated recombinant cells." *Trends in Biotech.* (1999) 17:78-83.
Chang, T.M., "Artificial liver support based on artificial cells with emphasis on encapsulated hepatocytes." *Artif Organs.* (1992) 16(1):71-4.
Davidson, B.L., et al., "A model system for in vivo gene transfer into the central nervous system using an adenoviral vector." *Nature Genetics* (1993) 3:219-223.
DeReuck, J. et al., "Steroid Treatment in Acute Ischemic Stroke." *Eur. Neurol.*, (1988) 28:70-72.
Douglas, J., et al., "A system for the propagation of adenoviral vectors with genetically modified receptor specificities." *Nature Biotech.* (1999) 17:470-475.
Dull, T., et al., "A third-generation lentivirus vector with a conditional packaging system." *J. Virol.* (1998) 72:8463-8471.
Frolov, I., et al. "Alphavirus-based expression vectors: Strategies and applications." *PNAS* (1996) 93:11371-11377.
Gluckman, E. et al., "Hematopoietic reconstitution in a patient with Fanconi's anemia by means of umbilical-cord blood from an HLA-identical sibling." *N. Engl. J. Med.*, (1989) 321(17):1174-1178.
Hofmann, C., et al., "Ovine adenovirus vectors overcome preexisting humoral immunity against human adenoviruses in vivo." *J. Virol.* (1999) 73:6930-6936.
Johnston, S.A., et al., "The use of microparticle injection to introduce genes into animal cells in vitro and in vivo." *Genet. Eng.* (1993) 15:225-236.
Kafri, T., et al., "A packaging cell line for lentivirus vectors." *J. Virol.* (1999) 73:576-584.
Knudtzon, S. "In vitro growth of granulocytic colonies from circulating cells in human cord blood." *Blood*, (1974) 43(3):357-361.
Laquerre, S., et al., "Recombinant Herpes Simplex Virus Type 1 Engineered for Targeted Binding to Erythropoietin Receptor-Bearing Cells." *J. Virol.* (1998) 72:9683-9697.

(Continued)

*Primary Examiner* — Valarie Bertoglio
(74) *Attorney, Agent, or Firm* — Viksnins Harris & Padys PLLP

(57) ABSTRACT

The invention relates generally to methods for isolation and culture of umbilical cord blood stem cells, cells isolated by the methods, and therapeutic uses for those cells.

15 Claims, 9 Drawing Sheets

OTHER PUBLICATIONS

Loeffler, J. et al. "Gene transfer into primary and established mammalian cell lines with lipopolyamine-coated DNA." *Methods in Enzymology* (1993) 217:599-618.

Lu, D. et al., "Intravenous administration of human umbilical cord blood reduces neurological deficit in the rat after traumatic brain injury." *Cell Transplantation*, (2002) 11(3);275-281.

Martin, F., et al. "Retrovirus Targeting by Tropism Restriction to Melanoma Cells." *J. Virol.* (1999) 73: 6923-6929.

Matthew, H.W., et al., "Microencapsulated hepatocytes. Prospects for extracorporeal liver support." *ASAIO Trans.* (1991) 37(3):M328-30.

Mochizuki, H., et al., "High-Titer Human Immunodeficiency Virus Type 1-Based Vector Systems for Gene Delivery into Nondividing Cells." *J. Virol.* (1998) 72:8873-8883.

Molin, M., et al., "Two Novel Adenovirus Vector Systems Permitting Regulated Protein Expression in Gene Transfer Experiments." *J. Virol.* (1998) 72:8358-8361.

Nakahata, T. et al. "Hemopoietic colony-forming cells in umbilical cord blood with extensive capability to generate mono- and multipotential hemopoietic progenitors." *J. Clin. Invest.*, (1982) 70(6):1324-1328.

Persons, D., et al., "Use of the green fluorescent protein as a marker to identify and track genetically modified hematopoietic cells." *Nature Medicine* (1998) 4:1201-1205.

Salmons, B., et al. "Targeting of Retroviral Vectors for Gene Therapy," *Hum. Gene Therapy* (1993) 4:129-141.

Sanberg, P.R. et al. "Potential of umbilical cord blood cells for brain repair." *J. Neurochemistry*, (2002) 81(5):83.

Sanberg, P.R. et al. "Intravenous administration of human umbilical cord blood stem cells improves stroke and traumatic brain injury in rats." *Neurosci. Abstr.*, (2001) 27:632.

Schwarzenberger, P., et al., "Receptor-targeted recombinant adenovirus conglomerates: a novel molecular conjugate vector with improved expression characteristics." *J. Virol.* (1997) 71:8563-8571.

Sebestyen, et al. "DNA vector chemistry: the covalent attachment of signal peptides to plasmid DNA." *Nature Biotech.* (1998) 16:80-85.

Shea, et al. "DNA delivery from polymer matrices for tissue engineering." *Nature Biotechnology* (1999) 17:551-554.

Sutton, R., et al., "Human immunodeficiency virus type 1 vectors efficiently transduce human hematopoietic stem cells." *J. Virol.* (1998) 72:5781-5788.

Wadlow, R.C., et al. "Umbilical cord blood transplantation: where do we stand?" *Biol. Of Blood and Marrow Transplantation*, (2002) 8:637-647.

Wagner, E., et al., "Coupling of Adenovirus to Transferrin-Polylysine/DNA Complexes Greatly Enhances Receptor-Mediated Gene Delivery and Expression of Transfected Genes." *PNAS* (1992) 89:6099-6103.

Wass, C. T. et al., "Insulin treatment of corticosteroid-associated hyperglycemia and its effect on outcome after forebrain ischemia in rats." *Anesthesiology*, (1996) 84(3):644-651.

Williams, R.S., et al., "Introduction of foreign genes into tissues of living mice by DNA-coated microprojectiles." *PNAS* (1991) 88:2726-2730.

Xiong, C., et al. "Sindbis virus: an efficient, broad host range vector for gene expression in animal cells." *Science* (1989) 243:1188-1191.

Yanagi, K., et al., "Performance of a new hybrid artificial liver support system using hepatocytes entrapped within a hydrogel." *ASAIO Trans.* (1989) 35(3):570-2.

Yang, N.S., et al., "In vivo and in vitro gene transfer to mammalian somatic cells by particle bombardment." *PNAS* (1990) 87:9568-9572.

Yang, N. S. et al., "Gene transfer via particle bombardment: Application of the Accell gene gun." In *Gene therapeutics : methods and applications of direct gene transfer.* Wolff, J. ed. Boston:Birkhäuser, (1994), p. 195.

International Search Report from PCT/US2005/017373, mailed Dec. 1, 2005.

Chen et al., "Intravenous administration of human umbilical cord blood reduces behavioral deficits after stroke in rats", *Stroke*, 32(11), 2682-2688 (2001).

Janowski et al., "Intra-carotid administration of neural progenitors derived from human umbilical cord blood mononuclear fraction gives robust behavioral recovery in ouabain model of stroke", *Experimental Neurology*, 187, p. 210, 11th Annual Conference of the American Society for Neural Transplantation and Repair (ASNTR), Clearwater Beach, FL, USA, May 6-9, 2004.

Low et al., "Characterization and transplantation of a novel population of umbilical cord blood stem cells" *Experimental Neurology*, 193, p. 251, 12th Annual Conference of the American Society of Neural Transplantation and Repair (ASNTR), Clearwater, FL, USA, Apr. 28-May 1, 2005.

Xiao et al., "Transplantation of a Novel Cell Line Population of Umbilical Cord Blood Stem Cells Ameliorates Neurological Deficits Associated with Ischemic Brain Injury," *Stem Cells and Development*, 14:722-733 (2005).

\* cited by examiner

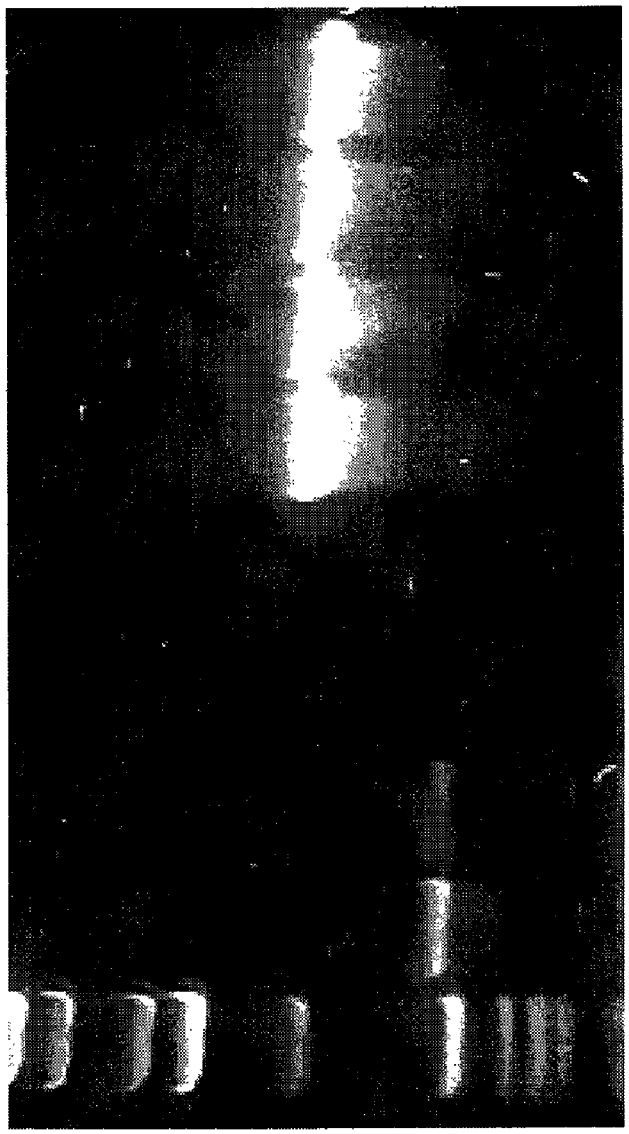

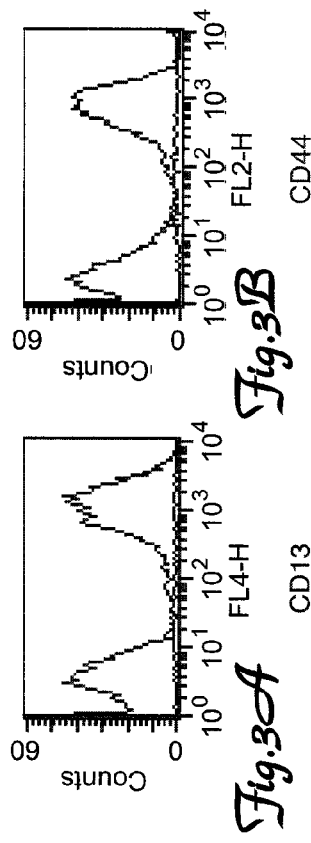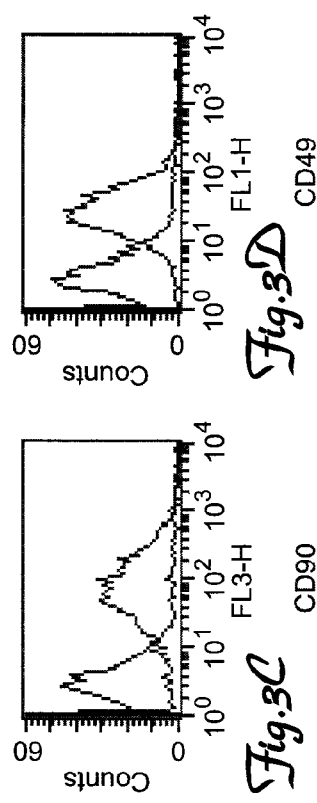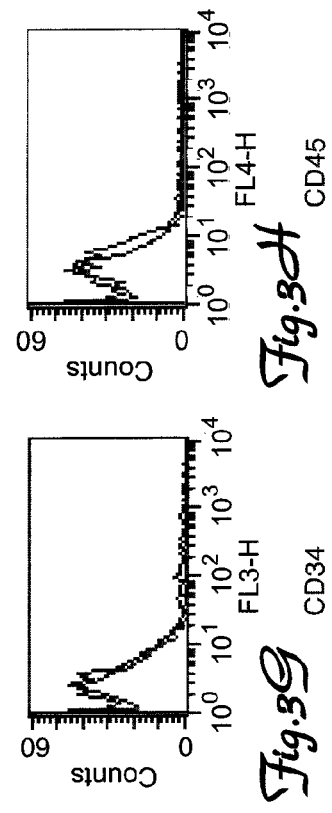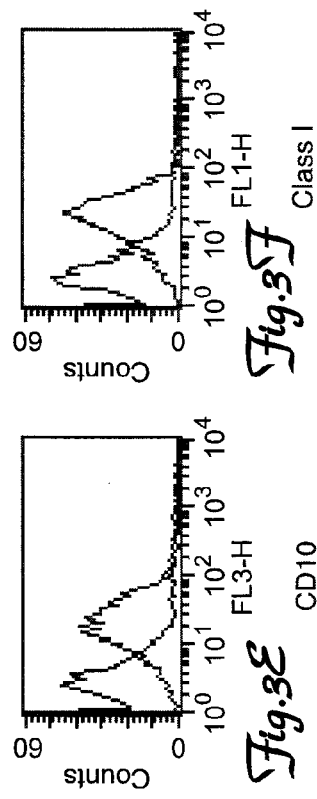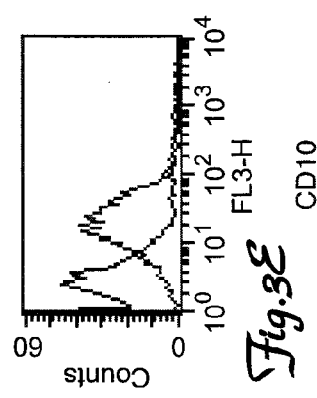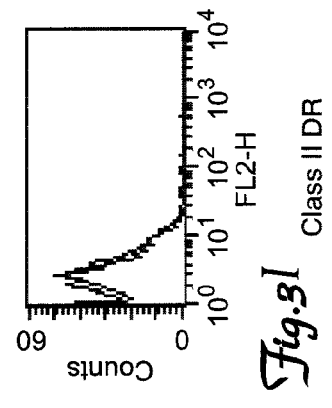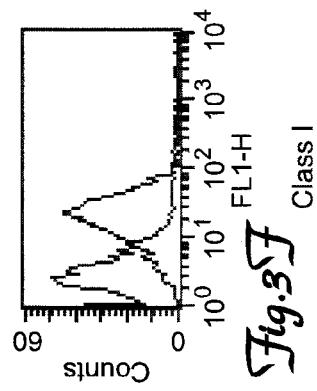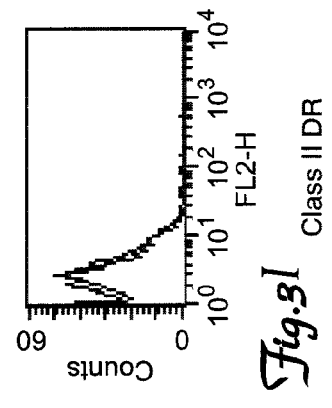
Fig. 3A CD13; Fig. 3B CD44; Fig. 3C CD90; Fig. 3D CD49; Fig. 3E CD10; Fig. 3F Class I; Fig. 3G CD34; Fig. 3H CD45; Fig. 3I Class II DR

SEQUENCE LISTING

<160> NUMBER OF SEQ ID NOS: 4

<210> SEQ ID NO 1
<211> LENGTH: 18
<212> TYPE: DNA
<213> ORGANISM: Homo sapiens

<400> SEQUENCE: 1
gaccagttct gatgactc         18

<210> SEQ ID NO 2
<211> LENGTH: 18
<212> TYPE: DNA
<213> ORGANISM: Homo sapiens

<400> SEQUENCE: 2
gtaggtggtg tatttctg          18

<210> SEQ ID NO 3
<211> LENGTH: 26
<212> TYPE: DNA

```
<213> ORGANISM: Homo sapiens

<400> SEQUENCE: 3
tgaaggtcgg agtcaacgga tttggt                                              26

<210> SEQ ID NO 4
<211> LENGTH: 24
<212> TYPE: DNA
<213> ORGANISM: Homo sapiens

<400> SEQUENCE: 4
catgtgggcc atgaggtcca ccac                                                24
```

USE OF UMBILICAL CORD BLOOD STEM CELLS TO TREAT ISCHEMIC EVENT

REFERENCE TO RELATED APPLICATIONS

This application claims priority under 35 U.S.C. 119(e) from U.S. Provisional Application Ser. No. 60/572,162 filed May 17, 2004, which is incorporated herein by reference.

STATEMENT OF GOVERNMENT RIGHTS

This work was funded by United States Grant No. R01-NS40831 from the National Institutes of Health. The government may have certain rights to this invention.

BACKGROUND OF THE INVENTION

Oxygen is supplied to the cells by the blood and most cellular energy production is tightly coupled to oxygen. Whenever the blood flow to an organ is interrupted, a state of ischemia exists. During ischemia, cellular ATP will be consumed and usually cannot adequately be replenished in the absence of a supply of oxygen. Ischemia can exist for only a portion of an organ when the blockage of the blood supply to the organ is not total. In addition to total ischemia, or no blood flow, there are intermediate degrees of ischemia.

Significant ischemia occurs in stroke and during most cases of open heart-surgery, all episodes of coronary occlusion or heart attack, all cases of organ transplantation, certain procedures such as liver shunt operations and a variety of other situations in which either significant stress or a period of shock has compromised the functioning of one or more organs of the body. In all of these situations, cellular energy metabolism is impaired, and its restoration is critical to the recovery of organ function.

For example, stroke, or cerebrovascular disease, is the name for several disorders that occur within seconds or minutes after the blood supply to the brain is disturbed. Stroke is the third leading cause of death in developed countries. Approximately 550,000 Americans suffer a stroke each year; one fourth of them die and half of the survivors have residual disabilities, including paralysis of face, extremities, speech disorders, loss of bladder function, inability to swallow or dementia. Stroke is the principal cause of severe disability, often requiring institutionalization of stroke survivors at a total cost in the U.S. of $20 to 30 billion dollars per year. Stroke is more likely to occur in the elderly, and the risk doubles each decade after age 35 years. Five percent of the population older than 65 years has had a stroke.

Symptoms of stroke may progress or fluctuate during the first day or two after onset; this is called evolution. When no further deterioration occurs, the condition is considered to be a completed stroke. The only warning signal that suggests susceptibility to a stroke is a transient ischemic attack (TIA).

Strokes are characterized by the location and type of disturbance. The most common is a deficient supply of blood through an artery (ischemia). About 84% of strokes (about 400,000 per year in the U.S.) result from occlusion of cerebral arteries by blood clots. Ischemic cell damage follows rapidly upon interruption of the blood supply downstream from the clot. The remaining 16% of strokes are the result of intracerebral or subarachnoid hemorrhage. While hemorrhage induces other injurious events, ischemia resulting from the "short circuited" blood flow is still a significant factor in neuronal damage from hemorrhagic strokes.

Cell death occurs rapidly in the core region of a stroke, where blood flow is reduced to about 20% of normal. However, there is a larger area of potential injury, called the ischemic penumbra, where blood flow is reduced to a lesser extent. Cells in this region are endangered, but may not be irreversibly damaged. It is this penumbral area wherein neuroprotective agents may have their most beneficial effects in preventing cell damage and death due to ischemia and thereby reducing the incidence of long term disabilities.

Pharmacological intervention into the stroke process has not been successful. For example, studies evaluating the effectiveness of corticosteroids in the setting of head injury or global or focal brain ischemia have demonstrated either no improvement or a worsening of neurological outcome. See, for example, C. T. Wass et al., *Anesthesiology*, 84, 644 (1996) and references cited therein. A study of stroke patients treated primarily with dexamethasone or methylprednisolone showed no significant difference in outcome between steroid and non-steroid treated patients. J. DeReuck et al., *Eur. Neurol.*, 28, 70 (1988). Chopp et al. have disclosed the use of progestins to treat stroke using stroke models in animals. (See U.S. Pat. No. 6,245,757.)

Due to the lack of available pharmacotherapeutic agents, a significant percentage of the population subject to stroke or its aftereffects are poorly managed. None of the drugs presently available are capable of preventing damage due to stroke and most, such as anticoagulants, which can be shown to speed clot dissolution and hasten reperfusion if given within three hours of the onset of ischemia, have disturbing side effects. Anticoagulants can in fact be fatal if used inappropriately, e.g., for treating a hemorrhagic stroke. Clearly, current therapy has failed to "seize control" of this debilitating pathology.

Human umbilical cord blood (HUCB) has emerged as an alternative stem-cell source for reconstituting the bone marrow and immune systems of patients treated with myeloablative chemotherapy or radiation. See, e.g., J. N. Barker et al., *Nature Revs.*, 3, 562 (2003). The presence of mature and primitive hematopoietic progenitor cells in umbilical cord blood was demonstrated by Knudtzon, *Blood*, 43, 357 (1974) and Nakahata and Ogawa, *J. Clin. Invest.*, 70, 1324 (1982), respectively. Experimental and clinical evidence demonstrating the feasibility of using UCB in lieu of bone marrow transplantation was later provided by Broxmeyer et al., *Proc. Natl. Acad. Sci. USA*, 86, 3828 (1989) and Gluckman et al., *N. Engl. J. Med.*, 321, 1174 (1989). The presence of CD34$^+$ progenitor cells and their ability to differentiate along a hematopoietic lineage is well documented.

P. R. Sandberg et al., *Neurosci. Abstr.*, 27, 632 (2001) have investigated whether intravenously infused human umbilical cord blood cells (HUCBC) enter the brain, survive, and improve neurological functional recovery after stroke or traumatic brain injury (TBI) in rats. In the experimental groups, HUCBC were injected into the tail vein at least 24 hours after stroke or TBI. Behavioral impairments were reported to be significantly improved as early as 14 days in both TBI and stroke animals, compared to controls. Injected cells entered brain and migrated into the parenchyma of the injured brain. The number of MAB1281 positive cells in the ipsi-lateral hemisphere were at least 3 times greater than in the contralateral side. Some of the cells expressed the neuronal markers, the astrocytic marker GFAP, and the endothelial cell marker FVIII. Sandberg et al. reported significant HUCBC in vivo migration to the brain tissue 24 hrs after injury, when compared to normal tissue. See also, P. R. Sandberg et al., *J. Neurochemistry*, 81(5), 83 (2002); D. Lu et al., *Cell Transplantation*, 11, 275 (2002); J. Chen et al., *Stroke*, 32, 2682 (2001). However, the factors and/or cellular populations that

SUMMARY OF THE INVENTION

The present invention provides an isolated human umbilical cord blood stem cell (hUCBSC) that is positive for the Oct-4 transcription factor (Oct-4$^+$), a characteristic of multipotent stem cells (MPSCs), and that are surface antigen negative for CD34 (CD34$^-$), a marker that is typically seen on hematopoietic stem cells (HSC). The hUCBSCs of the invention are also CD13$^+$, CD44$^+$, CD90$^+$, CD49$^+$, CD10$^+$ and MHC Class I positive (HLA I$^+$). In contrast, the hUCBSCs of the invention do not express CD34, CD45 and MHC Class II molecules (HLA II$^-$). This cell surface profile is distinct from cells classified as HSCs or as multipotent adult progenitor cells (MAPCs or MASCs). See, e.g., L. T. Furcht et al., published PCT applications nos. WO 01/11011 and WO 02/064748. The MAPCs/MASCs disclosed therein are reported to be Oct-4$^+$, but CD44$^-$ and HLA I$^-$, inter alia. Additionally, the UCBSCs of the present invention may also be multipotent, meaning that they may have the ability to give rise to cells having lineages of all three primitive germ layers (endoderm, mesoderm and ectoderm).

The present invention provides a method to treat cell/tissue damage due to ischemia, as caused by stroke, infarct or traumatic injury comprising administering to a mammal afflicted with ischemic cell damage, an effective amount of a pharmaceutical composition comprising a population of the UCBSCs of the invention, such as an expanded (e.g., cell propagation without differentiation) population of adherent mononuclear cells from UCB, in combination with a pharmaceutically acceptable liquid delivery vehicle, following onset of ischemia. The amount of cells is effective to ameliorate or mitigate at least one of the effects of ischemia, including ischemia resulting from the acute phase of stroke, traumatic brain injury or myocardial or pulmonary infarction or their aftereffects, such as those described hereinabove. It is believed that the present method functions, at least in part, by the ability of the cells to reduce the damage caused by ischemia, i.e., the brain damage caused by cerebral ischemia, and its aftereffects. The efficacy of the present method may also be due to differentiation of the multipotent UCBSCs into neuronal cells and other types of cells in situ.

The cells of the invention have been maintained in culture for over 80 population doublings. Evaluation of the molecules expressed on the surface membrane of these cells, confirmed the absence of CD34 molecules that are typically seen on hematopoietic stem cells (HSCs). In addition, the presence of other markers was found that are not seen on multipotent adult progenitor cells (MAPCs) derived from bone marrow and other areas of the body. Therefore, these cells represent a unique stem cell population within umbilical cord blood.

Tail vein infusion of these novel umbilical cord blood stem cells 48 hours after ischemic brain injury resulted in the amelioration of neurological deficits. These results demonstrate that a novel cell population found within umbilical cord blood can be used to treat patients that have experienced a stroke or other event that produces ischemic brain injury.

BRIEF DESCRIPTION OF THE FIGURES

FIG. 2 is a gel showing the presence of Oct-4 stem cell transcription factor mRNA in human UCBSCs. Lane M—ladder of molecular weights. Lanes 1-4 represent Oct-4 expression in (1) UCBSCs from subject 1, (2) UCBSCs from subject 2, (3) human liver, (4) human endothelial cells. Note presence of Oct-4 expression in umbilical cord stem cell samples, and absence of expression in differentiated liver and endothelial cells. Lanes 5 to 8 represent expression of G3PDH housekeeping gene in (5) UCBSCs from subject 1, (6) UCBSCs from subject 2, (7) human liver, and (8) human endothelial cells. Note presence of G3PDH expression in all cell types.

FIG. 3 (panels a-i) are flow cytometric graphs evaluating the expression of various cell surface molecules by hUCBSCs.

DETAILED DESCRIPTION OF THE INVENTION

Definitions

Figure 1:
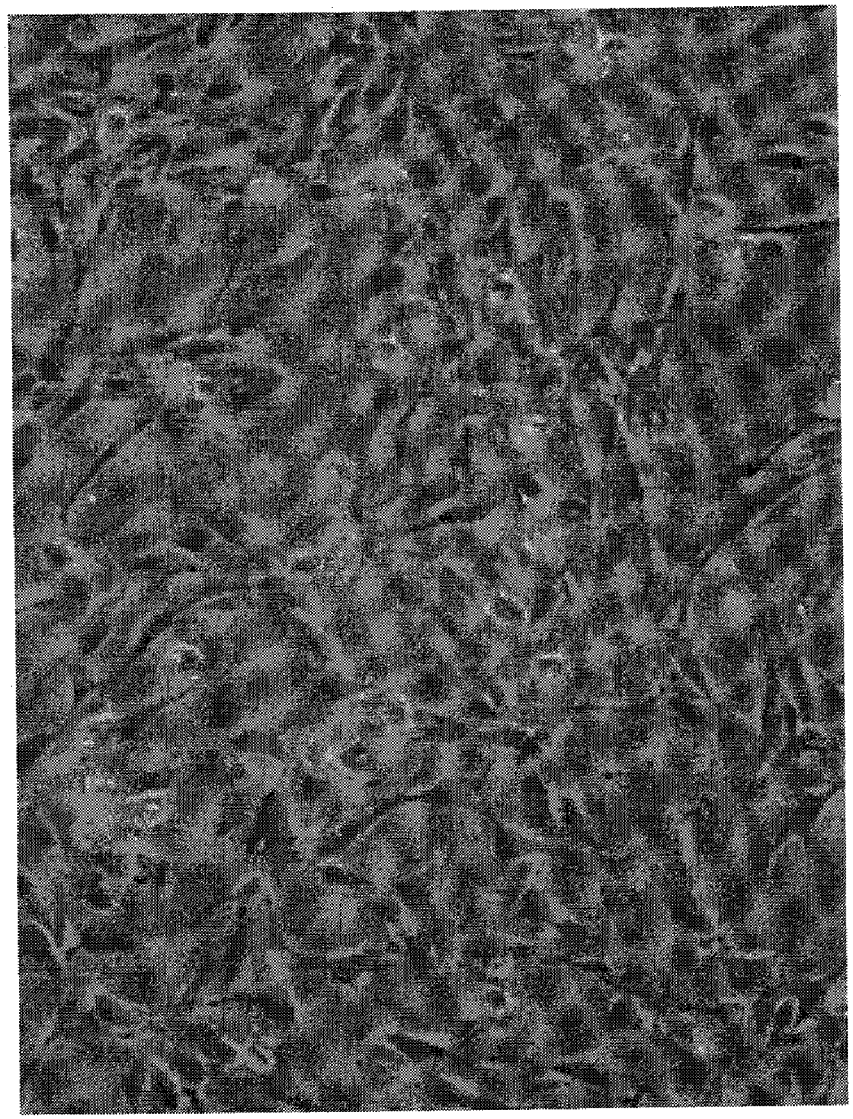
FIG. 1. Human umbilical cord stem cells in culture.

As used herein, the terms below are defined by the following meanings:

The term "isolated" refers to a cell or cells which are not associated with one or more cells or one or more cellular components that are associated with the cell or cells in vivo.

A "subject" is a vertebrate, preferably a mammal, more preferably a human. Mammals include, but are not limited to, humans, farm animals, sport animals and pets.

As used herein, "treat," "treating" or "treatment" includes treating, preventing, ameliorating, repairing (e.g., to restore, partially or fully, tissue function and/or condition after damage or injury) or inhibiting an injury or disease related condition and/or a symptom of an injury or disease related condition. In one embodiment, damaged neuronal tissue (e.g., tissue comprising neurons, such as any of the impulse-conducting cells that constitute the brain, spinal column, and nerves, consisting of a nucleated cell body with one or more dendrites and a single axon) refers to neuronal tissue that has as a result of disease (e.g., stroke) or trauma (e.g., biological, physical or surgical trauma), is reduce in function and/or mass.

An "effective amount" generally means an amount which provides the desired local or systemic effect, such as enhanced performance. For example, an effective dose is an amount sufficient to affect a beneficial or desired clinical result. Said dose could be administered in one or more administrations and could include any preselected amount of cells. The precise determination of what would be considered an effective dose may be based on factors individual to each subject, including their size, age, injury and/or disease being treated and amount of time since the injury occurred or the disease began. One skilled in the art, specifically a physician, would be able to determine the number of cells that would constitute an effective dose.

The terms "comprises", "comprising", and the like can have the meaning ascribed to them in U.S. Patent Law and can mean "includes", "including" and the like. As used herein, "including" or "includes" or the like means including, without limitation.

Administration of UCBSCs

UCBSCs or their differentiated progeny can be administered to a subject by a several methods available to the art, including but not limited to localized injection, catheter administration, systemic injection, intraperitoneal injection, parenteral administration, intracranial injection, intra-arterial injection, intravenous injection, intraplacental injection, intrauterine injection, intrathecal administration, intraventricular administration, intracisternal administration, intrastriatal administration, intranigral administration, intramuscular injection, surgical injection into a tissue of interest or via direct application to tissue surfaces (e.g., during surgery or on a wound).

A method to potentially increase cell survival is to incorporate UCBSCs or other cells of interest into a biopolymer or synthetic polymer. Depending on the patient's condition, the site of injection might prove inhospitable for cell seeding and growth because of scarring or other impediments. Examples of biopolymer include, but are not limited to cells mixed with fibronectin, fibrin, fibrinogen, thrombin, collagen, and proteoglycans. This could be constructed with or without included cytokines, differentiation factors, angiogenesis factors and/or anti-apoptosis factors. Additionally, these could be in suspension. Another alternative is a three-dimension gel with cells entrapped within the interstices of the cell biopolymer admixture. Again cytokines, differentiation factors, angiogenesis factors and/or anti-apoptosis factors could be included within the gel. These could be deployed by injection via various routes described herein, via catheters or other surgical procedures.

The quantity of cells to be administered will vary for the subject being treated. In a preferred embodiment, between about $10^3$ to about $10^9$, more preferably about $10^4$ to about $10^8$, more preferably about $10^5$ to about $10^7$ and most preferably about $10^7$ UCBSCs can be administered to a human subject. The precise determination of what would be considered an effective dose may be based on factors individual to each patient, including their size, age, disease or injury, size of damage caused by the disease or injury and amount of time since the damage occurred.

When administering a therapeutic composition of the present invention, it will generally be formulated in a unit dosage injectable form (solution, suspension, emulsion). The doses may be single doses or multiple doses over a period of several days. The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, UCBSCs can be administered initially, and thereafter maintained by further administration of UCBSCs. For instance, UCBSCs can be administered by one method of injection, and thereafter further administered by a different or the same method.

Examples of compositions comprising UCBSCs or differentiated progeny thereof, include liquid preparations for administration, including suspensions; and, preparations for direct or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, PVA, ethyl cellulose, hydroxypropyl cellulose, carbomer, and the like. The preferred concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. Preferably, they will not affect the viability or efficacy of the cells as described in the present invention.

Compositions can be administered in dosages and by techniques available to those skilled in the medical and veterinary arts taking into consideration such factors as the age, sex, weight, and condition of the particular subject, and the composition form used for administration (e.g., solid vs. liquid).

Matrices are also used to deliver cells of the present invention to specific anatomic sites, where particular growth factors incorporated into the matrix, or encoded on plasmids incorporated into the matrix for uptake by the cells, can be used to direct the growth of the initial cell population. DNA can be incorporated within pores of the matrix, for example, during the foaming process used in the formation of certain polymer matrices. As the polymer used in the foaming process expands, it entraps the DNA within the pores, allowing controlled and sustained release of plasmid DNA. Such a method of matrix preparation is described by Shea, et al. (*Nature Biotechnology* (1999) 17: 551-554).

Plasmid DNA encoding cytokines, growth factors, or hormones can be trapped within a polymer gene-activated matrix carrier, as described by Bonadio, J., et al. (*Nature Medicine* (1999) 5: 753-759). The biodegradable polymer is then implanted near the brain or other neural tissue, where UCBSCs are implanted and take up the DNA, which causes the UCBSCs to produce a high local concentration of the cytokine, growth factor, or hormone, accelerating healing of the damaged tissue.

In some embodiments, the UCBSCs are encapsulated. One goal in encapsulation in cell therapy is to protect allogeneic and xenogeneic cell transplants from destruction by the host immune response, thereby eliminating or reducing the need for immuno-suppressive drug therapy. Techniques for microencapsulation of cells are available to the art (see, for example, Chang, P., et al., *Trends in Biotech*. 1999; 17:78-83; Matthew, H. W., et al., ASAIO Trans. 1991; 37(3):M328-30; Yanagi, K., et al., *ASAIO Trans*. 1989; 35(3):570-2; Cai Z. H., et al., *Artif Organs*. 1988; 12(5):388-93; Chang, T. M., *Artif Organs*. 1992; 16(1):71-4). Materials for microencapsulation of cells include, for example, polymer capsules, dendrimer, liposome, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. U.S. Pat. No. 5,639,275, for example, describes improved devices and methods for long-term, stable expression of a biologically active molecule using a biocompatible capsule containing genetically engineered cells.

For the purposes described herein, either autologous, allogeneic or xenogenic UCBSCs of the present invention can be administered to a subject, either in differentiated or undifferentiated form, genetically altered or unaltered, by direct injection to a desired site, systemically, on or around the surface of an acceptable matrix, or in combination with a pharmaceutically acceptable carrier.

Monitoring of Subjects After Administration of UCBSCs

Following transplantation, the growth and/or differentiation of the administered UCBSCs or their differentiated progeny, and the therapeutic effect of the UCBSCs or progeny may be monitored. For example, the functionality of UCBSCs administered to treat damaged neuronal tissue may be monitored by analyzing behavioral studies before an after administration of the UCBSCs.

Following administration, the immunological tolerance of the subject to the UCBSCs or progeny derived therefrom may be tested by various methods known in the art to assess the subject's immunological tolerance to UCBSCs or progeny derived therefrom. In cases where subject's tolerance of UCBSCs or progeny derived therefrom is suboptimal (e.g., the subject's immune system is rejecting the exogenous UCBSCs), therapeutic adjunct immunosuppressive treatment, which is available to the art, of the subject may be performed.

Genetically-Modified UCBSCs

UCBSCs or their differentiated progeny can be genetically altered ex vivo, and thereby produce a transgenic UCBSCs. For example, a subject's umbilical cord blood is obtained and UCBSCs are isolated. The UCBSCs are then genetically altered to express one or more preselected gene products. The UCBSCs can then be screened or selected ex vivo to identify those cells which have been genetically altered, and these cells can be introduced into a subject or can be differentiated and introduced into a subject, either locally or systemically. Alternately, UCBSCs can be differentiated and then the differentiated cells can be genetically altered prior to administration.

Thus, transplanted genetically modified UCBSCs can provide an preselected gene product. Genetically-modified UCBSCs or their genetically-modified differentiated progeny are useful in the methods of the invention, for example, to provide a gene product to a desired tissue (e.g., neural tissue, including brain and spinal cord tissue).

UCBSCs can be genetically modified by introducing preselected DNA or RNA (e.g., an exogenous nucleic acid) into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, nucleofection, or direct "naked" DNA transfer. Cells can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs; the antisense nucleic acid molecule can have a sequence which is complementary to the sequence of the portion of the cellular genome to be inactivated), or by ribozyme technology (with a ribozyme sequence directed to the sequence of the portion of the cellular genome to be inactivated), for example. In one embodiment, the portion of the cellular genome to be inactivated initiates, maintains or reverses a differentiation process. Insertion of one or more pre-selected DNA sequences can be accomplished by homologous or non-homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) for expression in specific cell compartments (including but not limited to the cell membrane). The techniques listed herein can also be applied to introduce a transcriptional regulatory sequence into UCBSCs to activate a desired endogenous gene.

Calcium phosphate transfection, which relies on precipitates of plasmid DNA/calcium ions, can be used to introduce plasmid DNA containing a target gene or polynucleotide into isolated or cultured UCBSCs. Briefly, plasmid DNA is mixed into a solution of calcium chloride, then added to a solution which has been phosphate-buffered. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e.g., ProFection® from Promega Corp., Madison, Wis.).

DEAE-dextran transfection, which is also known to those of skill in the art, may be preferred over calcium phosphate transfection where transient transfection is desired, as it is often more efficient.

Since the cells of the present invention are isolated cells, microinjection can be particularly effective for transferring genetic material into the cells. Briefly, cells are placed onto the stage of a light microscope. With the aid of the magnification provided by the microscope, a glass micropipette is guided into the nucleus to inject DNA or RNA. This method is advantageous because it provides delivery of the desired genetic material directly to the nucleus, avoiding both cytoplasmic and lysosomal degradation of the injected polynucleotide. This technique has been used effectively to accomplish germline modification in transgenic animals.

Cells of the present invention can also be genetically modified using electroporation. The target DNA or RNA is added to a suspension of cultured cells. The DNA/RNA-cell suspension is placed between two electrodes and subjected to an electrical pulse, causing a transient permeability in the cell's outer membrane that is manifested by the appearance of pores across the membrane. The target polynucleotide enters the cell through the open pores in the membrane, and when the electric field is discontinued, the pores close in approximately one to 30 minutes.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPC) can be added. A recommended reagent for liposomal transfer is Lipofectin® (Life Technologies, Inc.), which is commercially available. Lipofectin®, for example, is a mixture of the cationic lipid N-[1-(2,3-dioleyloyx)propyl]-N-N-N-trimethyl ammonia chloride and DOPE. Delivery of linear DNA, plasmid DNA, or RNA can be accomplished either in vitro or in vivo using liposomal delivery, which may be a preferred method due to the fact that liposomes can carry larger pieces of DNA, can generally protect the polynucleotide from degradation, and can be targeted to specific cells or tissues. A number of other delivery systems relying on liposomal technologies are also commercially available, including Effectene™ (Qiagen), DOTAP (Roche Molecular Biochemicals), FuGene 6™ (Roche Molecular Biochemicals), and Transfectam® (Promega). Cationic lipid-mediated gene transfer efficiency can be enhanced by incorporating purified viral or cellular envelope components, such as the purified G glycoprotein of the vesicular stomatitis virus envelope (VSV-G), in the method of Abe, A., et al. (*J. Virol.* (1998) 72: 6159-6163).

Gene transfer techniques which have been shown effective for delivery of DNA into primary and established mammalian cell lines using lipopolyamine-coated DNA can be used to introduce target DNA into UCBSCs. This technique is generally described by Loeffler, J. and Behr, J. (*Methods in Enzymology* (1993) 217: 599-618).

Naked plasmid DNA can be injected directly into a tissue mass formed of differentiated cells from the isolated UCBSCs. This technique has been shown to be effective in transferring plasmid DNA to skeletal muscle tissue, where expression in mouse skeletal muscle has been observed for more than 19 months following a single intramuscular injection. More rapidly dividing cells take up naked plasmid DNA more efficiently. Therefore, it is advantageous to stimulate cell division prior to treatment with plasmid DNA.

Microprojectile gene transfer can also be used to transfer genes into UCBSCs either in vitro or in vivo. The basic procedure for microprojectile gene transfer was described by J. Wolff (*Gene Therapeutics* (1994) at page 195). Briefly, plasmid DNA encoding a target gene is coated onto microbeads, usually 1-3 micron sized gold or tungsten particles. The coated particles are placed onto a carrier sheet inserted above a discharge chamber. Once discharged, the carrier sheet is accelerated toward a retaining screen. The retaining screen forms a barrier which stops further movement of the carrier sheet while allowing the polynucleotide-coated particles to be propelled, usually by a helium stream, toward a target surface, such as a tissue mass formed of differentiated UCBSCs. Microparticle injection techniques have been described previously, and methods are known to those of skill in the art (see Johnston, S. A., et al., *Genet. Eng.* (NY) (1993) 15: 225-236; Williams, R. S., et al., *Proc. Natl. Acad. Sci. USA* (1991) 88: 2726-2730; Yang, N. S., et al., *Proc. Natl. Acad. Sci. USA* (1990) 87: 9568-9572).

Signal peptides can be attached to plasmid DNA to direct the DNA to the nucleus for more efficient expression (Sebestyen, et al. *Nature Biotech.* (1998) 16: 80-85).

Viral vectors can be used to genetically alter UCBSCs of the present invention and their progeny. Viral vectors are used, as are the physical methods previously described, to deliver one or more target genes, polynucleotides, antisense molecules, or ribozyme sequences, for example, into the cells. Viral vectors and methods for using them to deliver DNA to cells are well known to those of skill in the art. Examples of viral vectors which can be used to genetically alter the cells of the present invention include, but are not limited to, adenoviral vectors, adeno-associated viral vectors, retroviral vectors (including lentiviral vectors), alphaviral vectors (e.g., Sindbis vectors), and herpes virus vectors.

Retroviral vectors are effective for transducing rapidly-dividing cells, although a number of retroviral vectors have been developed to effectively transfer DNA into non-dividing cells as well (Mochizuki, H., et al., *J Virol*. (1998) 72: 8873-8883). Packaging cell lines for retroviral vectors are known to those of skill in the art. Packaging cell lines provide the viral proteins needed for capsid production and virion maturation of the viral vector. Generally, these include the gag, pol, and env retroviral genes. An appropriate packaging cell line is chosen from among the known cell lines to produce a retroviral vector which is ecotropic, xenotropic, or amphotropic, providing a degree of specificity for retroviral vector systems.

A retroviral DNA vector is generally used with the packaging cell line to produce the desired target sequence/vector combination within the cells. Briefly, a retroviral DNA vector is a plasmid DNA which contains two retroviral LTRs positioned about a multicloning site and SV40 promoter so that a first LTR is located 5' to the SV40 promoter, which is operationally linked to the target gene sequence cloned into the multicloning site, followed by a 3' second LTR. Once formed, the retroviral DNA vector can be transferred into the packaging cell line using calcium phosphate-mediated transfection, as previously described. Following approximately 48 hours of virus production, the viral vector, now containing the target gene sequence, is harvested.

Targeting of retroviral vectors to specific cell types was demonstrated by Martin, F., et al. (*J. Virol* (1999) 73: 6923-6929), who used single-chain variable fragment antibody directed against the surface glycoprotein high-molecular-weight melanoma-associated antigen fused to the amphotropic murine leukemia virus envelope to target the vector to delivery the target gene to melanoma cells. Where targeted delivery is desired, as, for example, when differentiated cells are the desired objects for genetic alteration, retroviral vectors fused to antibody fragments directed to the specific markers expressed by each cell lineage differentiated from the UCBSCs of the present invention can be used to target delivery to those cells.

Lentiviral vectors are also used to genetically alter cells of the invention. Many such vectors have been described in the literature and are available to those of skill in the art (Salmons, B. and Gunzburg, W. H., "Targeting of Retroviral Vectors for Gene Therapy," *Hum. Gene Therapy* (1993) 4: 129-141). These vectors have been effective for genetically altering human hematopoietic stem cells (Sutton, R., et al., *J. Virol*. (1998) 72: 5781-5788). Packaging cell lines have been described for lentivirus vectors (Kafri, T., et al., *J. Virol*. (1999) 73: 576-584; Dull, T., et al., *J. Virol*. (1998) 72: 8463-8471).

Recombinant herpes viruses, such as herpes simplex virus type I (HSV-1) have been used successfully to target DNA delivery to cells expressing the erythropoietin receptor (Laquerre, S., et al., *J. Virol*. (1998) 72: 9683-9697). These vectors can also be used to genetically alter the cells of the present invention, which the inventors have demonstrated to be stably transduced by a viral vector.

Adenoviral vectors have high transduction efficiency, can incorporate DNA inserts up to 8 Kb, and can infect both replicating and differentiated cells. A number of adenoviral vectors have been described in the literature and are known to those of skill in the art (Davidson, B. L., et al., *Nature Genetics* (1993) 3: 219-223; Wagner, E., et al., *Proc. Natl. Acad. Sci. USA* (1992)89: 6099-6103). Methods for inserting target DNA into an adenovirus vector are known to those of skill in the art of gene therapy, as are methods for using recombinant adenoviral vectors to introduce target DNA into specific cell types (Wold, W., Adenovirus Methods and Protocols, Humana Methods in Molecular Medicine (1998), Blackwell Science, Ltd.). Binding affinity for certain cell types has been demonstrated by modification of the viral vector fiber sequence. Adenovirus vector systems have been described which permit regulated protein expression in gene transfer (Molin, M., et al., *J. Virol*. (1998) 72: 8358-8361). A system has also been described for propagating adenoviral vectors with genetically modified receptor specificities to provide transductional targeting to specific cell types (Douglas, J., et al., *Nature Biotech*. (1999) 17: 470-475). Recently described ovine adenovirus vectors even address the potential for interference with successful gene transfer by preexisting humoral immunity (Hofmann, C., et al., *J. Virol*. (1999) 73: 6930-6936).

Adenovirus vectors are also available that provide targeted gene transfer and stable gene expression using molecular conjugate vectors, constructed by condensing plasmid DNA containing the target gene with polylysine, with the polylysine linked to a replication-incompetent adenovirus. (Schwarzenberger, P., et al., J. Virol. (1997) 71: 8563-8571.)

Alphavirus vectors, particularly the Sindbis virus vectors, are also available for transducing the cells of the present invention. These vectors are commercially available (Invitrogen, Carlsbad, Calif.) and have been described in, for example, U.S. Pat. No. 5,843,723, as well as by Xiong, C., et al. (Science (1989) 243: 1188-1191), Bredenbeek, P. J., et al. (J. Virol. (1993) 67: 6439-6446), and Frolov, I., et al. (*Proc. Natl. Acad. Sci. USA* (1996) 93: 11371-11377).

Successful transfection or transduction of target cells can be demonstrated using genetic markers, in a technique that is known to those of skill in the art. The green fluorescent protein of *Aequorea victoria*, for example, has been shown to be an effective marker for identifying and tracking genetically modified hematopoietic cells (Persons, D., et al., *Nature Medicine* (1998) 4: 1201-1205). Alternative selectable markers include the β-Gal gene, the truncated nerve growth factor receptor, drug selectable markers (including but not limited to NEO, MTX, hygromycin).

Kits Containing UCBSCs or UCBSC Isolation and Culture Components

UCBSCs of the present invention can be provided in kits, with appropriate packaging material. For example, UCBSCs can be provided as frozen stocks, accompanied by separately packaged appropriate factors and media, as previously described herein, for culture in the undifferentiated state. Additionally, separately packaged factors for induction of differentiation also be provided.

Kits containing effective amounts of appropriate factors for isolation and culture of a subject's cells are also provided by the present invention. Upon obtaining the umbilical cord blood from a subject, the clinical technician only need select the UCBSCs, using the method described herein, with the materials provided in the kit, then culture the cells as described by the method of the present invention, using culture medium supplied as a kit component. The composition of the basic culture medium has been described herein.

One aspect of the invention is the preparation of a kit for isolation of UCBSCs from a subject in a clinical setting. Using kit components packaged together, UCBSCs can be isolated from umbilical cord blood. Using additional kit components including differentiation factors, culture media, and instructions for isolating and/or inducing differentiation of UCBSCs in culture, a clinical technician can produce a population of undifferentiated or differentiated cells from the subject's own sample. Additional materials in the kit can provide vectors for delivery of polynucleotides encoding desired proteins for expression by the cells. Such vectors can be introduced into the cultured cells using, for example, calcium phosphate transfection materials, and directions for use, supplied with the kit. Additional materials can be supplied for injection of UCBSCs, including genetically-altered UCBSCs into the patient.

EXAMPLES

The following examples are provided in order to demonstrate and further illustrate certain embodiments and aspects of the present invention and are not to be construed as limiting the scope thereof.

Example 1

Isolation of a Novel of Human Umbilical Cord Stem Cells

Human umbilical cord blood (UCB) was collected after labor and delivery and placed into a blood bank pack unit (Baxter) that contained 35 ml of CPD (921 mg sodium citrate, 893 mg dextrose, 105 mg citric acid, 78 mg mono basic sodium phosphate). UCB samples were kept at room temperature and processed within 4 hours after harvesting. UCB was diluted 1:4 in phosphate-buffered saline (PBS) with 0.5% BSA. Mononuclear cells (MNCs) were separated by centrifugation (500 g, 30 minutes) in a Ficoll-Hypaque gradient (density 1.077 g/cm$^3$), suspended in PBS with 0.5% BSA and washed twice. $10 \times 10^6$ MNCs were plated in T25 cell culture flasks in 7 ml culture medium (DMEM/F12 (Invitrogen), 1×N2 serum-free supplement (Invitrogen), with 10% FBS (Invitrogen), 20 ng/ml b-FGF (R&D Systems), 20 ng/ml EGF (R&D Systems), 100 U penicillin (Invitrogen), and 1000 U streptomycin (Invitrogen)). About 15 to 18 days later, when adherent cells were more than 20% confluent, they were detached with 0.25% trypsin-EDTA (Invitrogen) and replated at a 1:2 dilution under the same culture conditions. For subculture, when cells were more than 60%-70% confluent, they were split at 1:3 under the same culture conditions except with 2% FBS. Under these conditions, these cells have been maintained beyond 80 population doublings (FIG. 1).

Example 2

Expression of Oct-4 Transcription Factor by Isolated Human Umbilical Cord Blood Stem Cells Oct-4 (also known as Oct-3/4) is a key transcription factor that is typically expressed by multipotent stem cells. At the present time Oct-4 expression by umbilical cord cells has not been reported in the scientific literature. To determine whether the cells isolated from cord blood express this stem cell transcription factor, mRNA was isolated from $5 \times 10^6$ cord blood stem cells (CBSCs). The mRNA was reverse transcribed and cDNA was amplified as follows: 95° C., 15 min., 35 cycles (94° C., 45 sec., 56° C., 45 sec., 72° C., 1 min.), followed by 72° C., 10 min. Primers used for Oct-4 (primers were designed using the "Oct-4" gene sequence as listed in GenBank accession number AJ297527) were (GACCAGT-TCTGATGACTC (SEQ ID NO:1); GTAGGTGGTG-TATTTCTG (SEQ ID NO:2)) and for G3PDH were (TGAAGGTCGGAGTCAACGGATTTGGT (SEQ ID NO:3); CATGTGGGCCATGAGGTCCACCAC (SEQ ID NO:4)). G3PDH was used as a housekeeping gene control.

FIG. 2 demonstrates the presence of Oct-4 stem cell transcription factor mRNA in human umbilical cord stem cells. Lane M—ladder of molecular weights. Lanes 1 to 4 represent Oct-4 expression in (1) UCBSCs from subject 1, (2) UCBSCs from subject 2, (3) human liver, and (4) human endothelial cells. Note presence of Oct-4 expression in umbilical cord stem cell samples, and absence of expression in differentiated liver and endothelial cells. Lanes 5 to 8 represent expression of G3PDH housekeeping gene in (5) UCBSCs from subject 1, (6) UCBSCs from subject 2, (7) human liver, and (8) human endothelial cells. Note presence of G3PDH expression in all cell types.

Example 3

Cell Surface Markers of Umbilical Cord Blood Stem Cells

To determine the cell surface markers expressed by UCBSCs, single cell suspensions of UCBSCs were incubated for 20 min. at 4° C. with the following antibodies purchased from BD Bioscience: CD34, CD45, CD90, CD13, CD44, CD49, CD10, Class I, Class II DR, and isotype controls. One hundred thousand events were acquired and analyzed in a flow cytometer (Becton Dickinson) using the CELLQUEST software. The UCBSCs were positive for CD13, CD44, CD90, CD49, CD10, and MHC Class I cell surface molecules (FIG. 3). In contrast, the UCBSCs did not express CD34, CD45, and MHC Class II molecules (FIG. 3). This cell surface profile is distinct from cells classified as hematopoietic stem cells (HSCs) and multipotent adult stem cells (MAPCs).

Example 4

Figure 4:
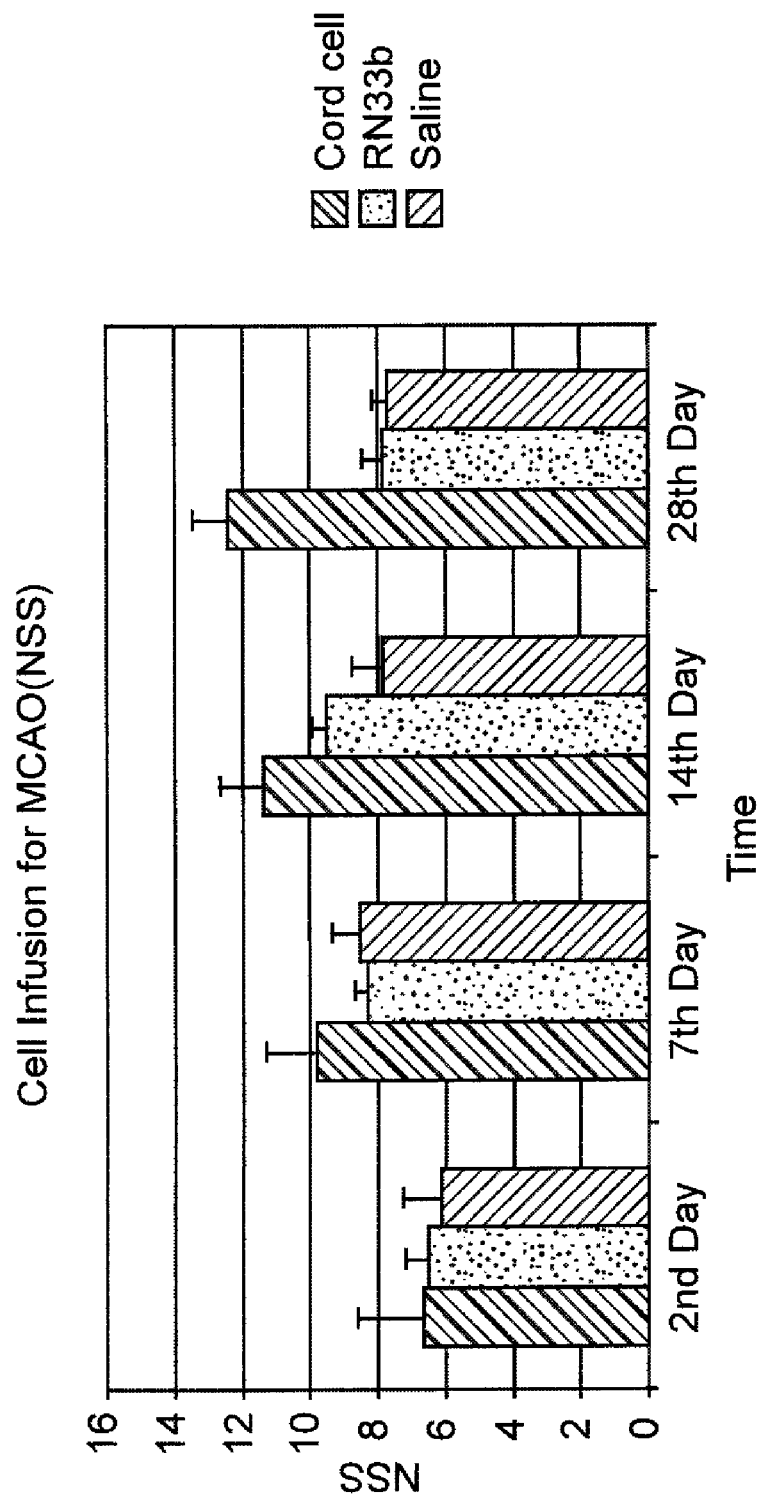
FIG. 4 is a graph depicting the effect of UCBSCs, RN33b cells and saline on a rat model of ischemic brain injury. Neurological severity scores (NSS) were evaluated in rats with ischemic brain treated with human umbilical cord blood stem cells ("Cord Cell" Group), RN33b neural stem cells ("RN33b" Group), or saline. Note, progressive and significant improvement by rats treated with umbilical cord stem cells.
Figure 5:
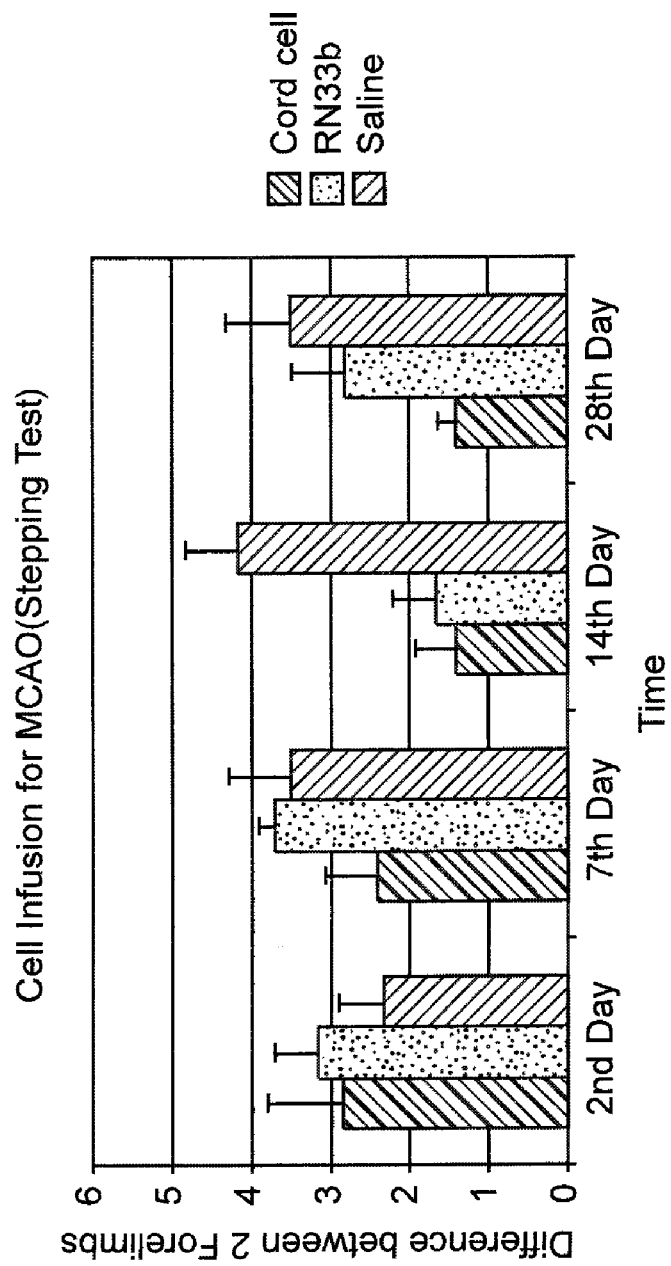
FIG. 5 is a graph depicting the effects of UCBSC transplants on stepping performance of rats with unilateral ischemic brain injury. The stepping behavior of rats with unilateral ischemic brain injury was tested in animals treated with umbilical cord stem cells ("Cord Cell" Group), RN33b neural stem cells ("RN33b" Group), or saline. Note, progressive improvement by the group treated with umbilical cord stem cells.
Figure 6:
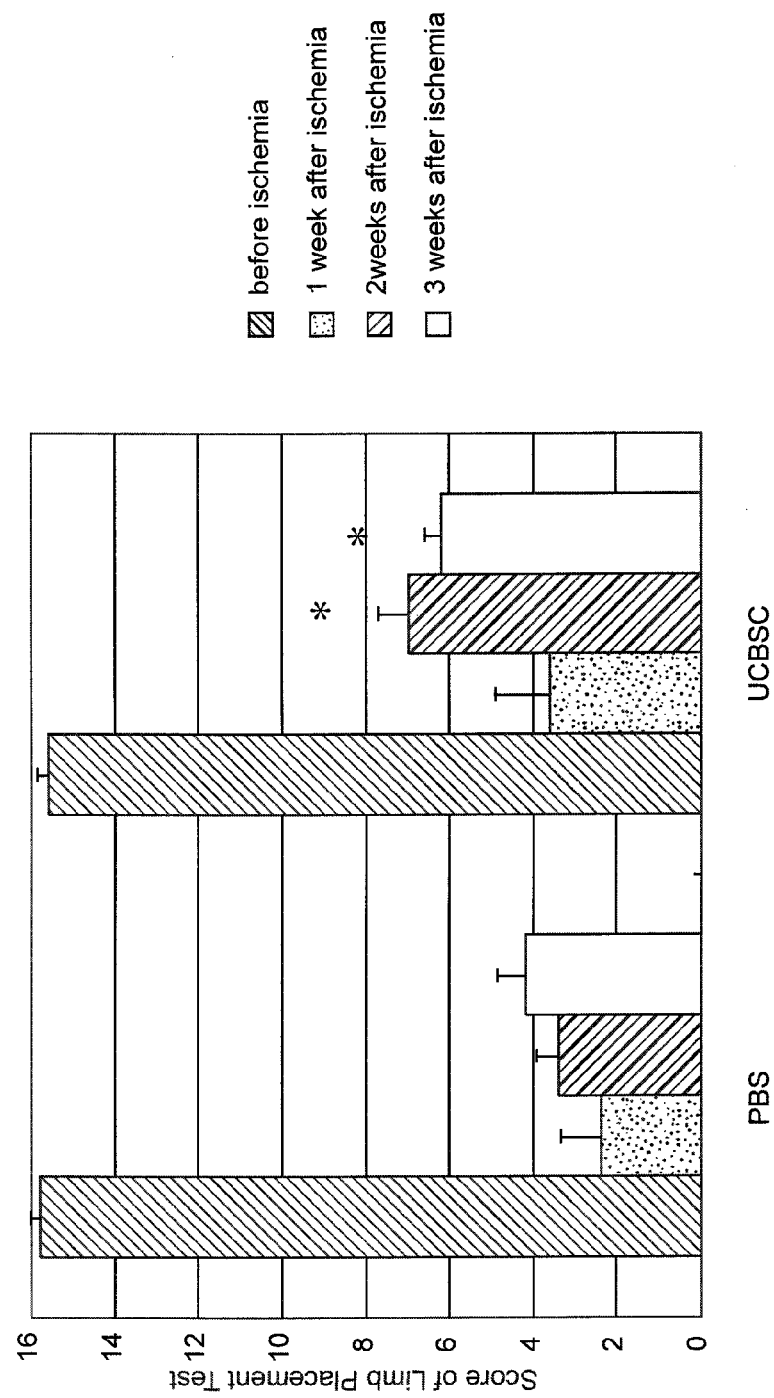
FIG. 6 a graph depicting the results of a limb placement test before ischemia and 1, 2 and 3 weeks after ischemia in rats treated with PBS (control) or UCBSCs. Behavioral evaluation. Data were analyzed with Mann-Whitney nonparametric test between groups at the same time point. *$p<0.05$. Data were presented as mean±SEM. These data demonstrate that transplanted human umbilical cord stem cells can ameliorate ischemia-induced neurological deficits.

Restorative Effects of Umbilical Cord Blood Stem Cell Transplants on Neurological Function To evaluate the potential use of this novel population of stem cells derived from human umbilical cord blood, the UCBSCs were administered by tail vein injection into a rodent model of ischemic brain injury. Reperfusion injury was induced in rats by the insertion of a thread up the middle cerebral artery to block blood flow to various regions of the brain and induce ischemia. The thread was then removed to induce reperfusion injury. Forty-eight hours after the induction of ischemic reperfusion brain injury, 1 million human umbilical blood stem cells were injected into the tail vein of each rat. Animals were tested for neurological function before the infusion of the umbilical cord stem cells, and at various time periods afterwards using a battery of behavioral tests.

a. Neurological deficit evaluation. Limb placement tests for the neurological evaluations included eight subtests described by Johansson and co-workers. Briefly, the four limbs of a rat were tested on a counter top surface and at its edges. For each subtest, an animal received a score of 0 if it was unable to place its limbs; a score of 1 if there was a partial and/or delayed (more than 2 sec) placement of its limbs; or a score of 2 if the animal exhibited an immediate and correct placement of its limbs. All scores are then summed to produce a neurological severity score. Animals treated with human UCBSCs exhibited mean scores greater than 12 at twenty-eight days after the ischemic injury and were significantly better than animals treated with RN33b rat neural stem cells and saline, where mean scores were lower than 8 (FIG. 4).

b. Stepping test. In the stepping test, animals were gently held so that only one forelimb extends freely from its body. The animal was then positioned so that the forelimb comes into contact with a bench top. As the suspended animal was moved forward along the bench top its forelimb will reflexly make a stepping movement. The number of stepping movements made by each animal was quantified over a distance of 100 cm for both the left and right forelimb. In normal animals the difference in stepping movements between the left and right forelimb is insignificant. Animals with ischemic stroke to one side of the brain, however, exhibit significantly fewer steps by the contralateral affected forelimb in comparison to the non-affected ipsilateral forelimb. FIG. 5 demonstrates that in animals treated with umbilical cord blood stem cells there was a progressive improvement in performance as revealed by decreases in the difference between left and right forelimb performance. In contrast, animals treated with RN33b neural stem cells or saline continued to exhibit differences in forelimb function over a period of 28 days of testing.

c. Behavioral evaluation. In FIG. 6, data for a limb placement test were analyzed with Mann-Whitney nonparametric tests between groups at the same time point (before ischemia and 1, 2 and 3 weeks after ischemia in rats treated with PBS (control) or UCBSCs). *$p<0.05$. Data were presented as mean±SEM. These data demonstrate that transplanted human umbilical cord blood stem cells can ameliorate ischemia-induced neurological deficits.

Example 5

Figure 7:
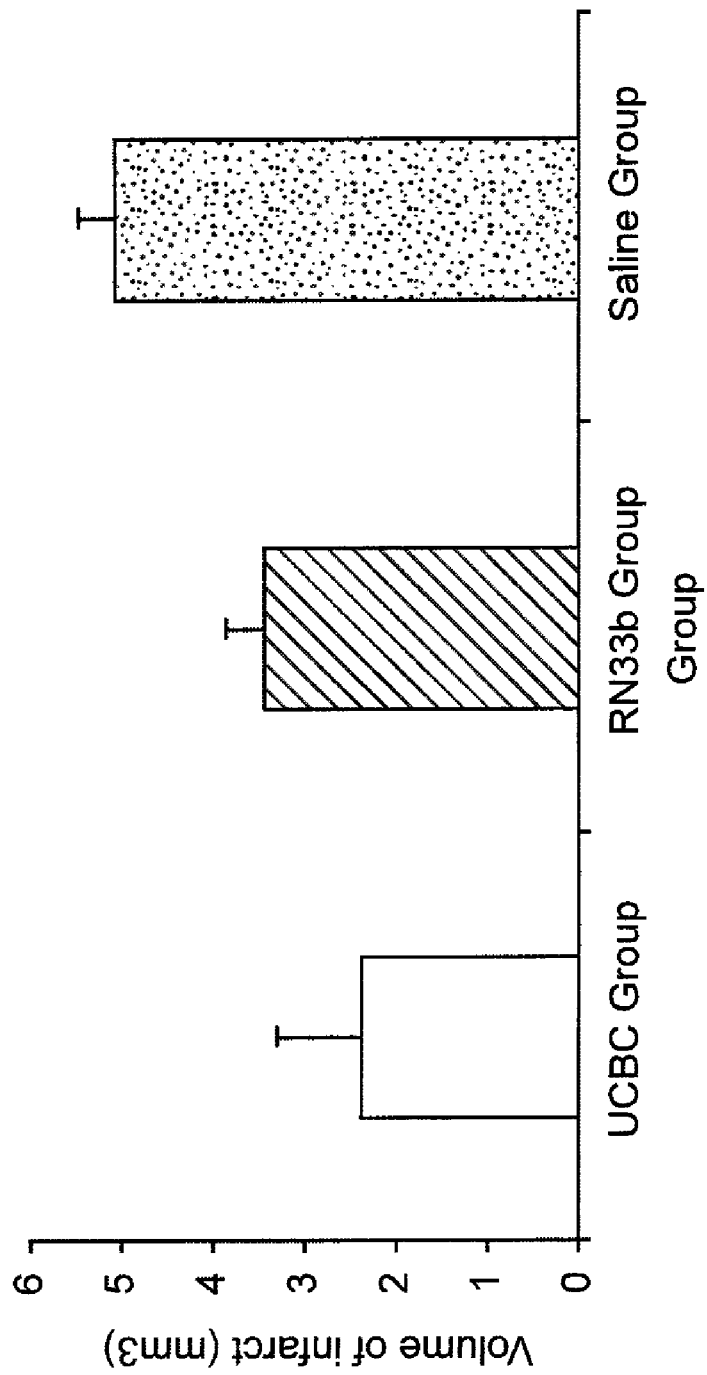
FIG. 7 is a graph depicting the results of administering cord blood stem cells (UCBSC), RN33b and saline to animals following ischemic brain injury. The results demonstrate that transplants of hUCBSCs can significantly reduce the size of cortical infarction following ischemic brain injury.

Effects of Umbilical Cord Blood Stem Cell Transplants on Reducing Brain Lesion Volume The effect of transplanting cord blood stem cells to minimize the size of the ischemia-induced cerebral infarct volume size is shown in FIG. 7. Animals treated with cord blood stem cells had cortical infarct sizes less than half that exhibited by saline control animals ($p<0.05$). These results demonstrate that transplants of human cord blood stem cells can significantly reduce the size of cortical infarction following ischemic brain injury.

Example 6

Figure 8A:
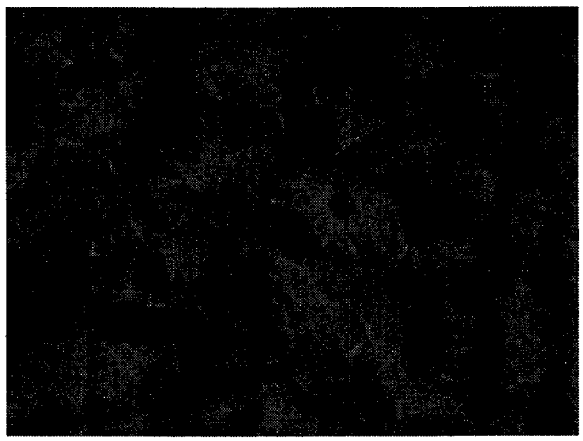
FIG. 8 depicts the representative finding of the dorsolateral striatum ipsilateral to the ischemic lesion (A-B). A. PBS injected animal. B. UCBSC injected animal. Scale bar=200 µm. C. Ratio of density of ipsilateral/contralateral axons to the ischemia were analyzed with unpaired t-test. *$p<0.05$. Data is shown as mean±SEM. These data demonstrate the sprouting of host nerve fibers as a result of transplanting human umbilical cord stem cells.
Figure 8B:
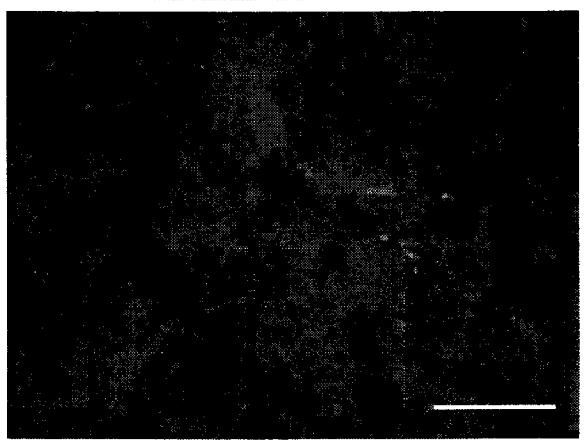
Figure 8C:
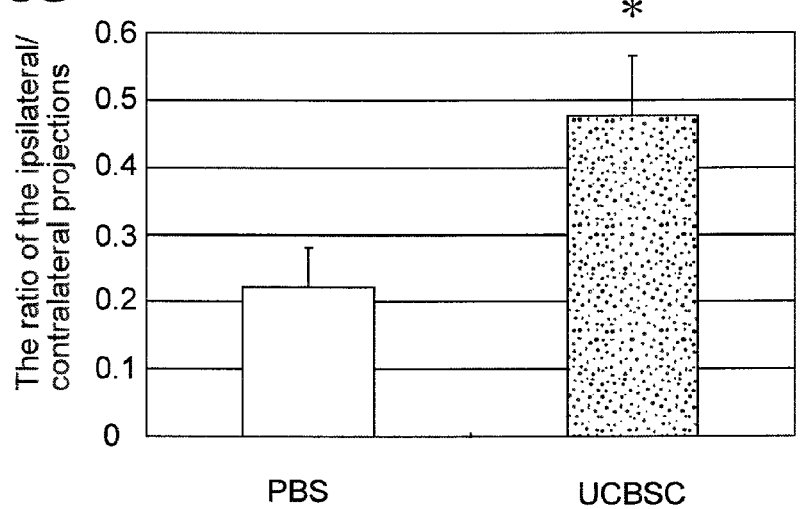

Effects of Umbilical Cord Blood Stem Cells on Sprouting of Host Nerve Fibers in Ischemic Brain Injury Through analysis of dorsolateral striatum ipsilateral to the ischemic lesion in PBS and UCBSC injected animals and determination of the ratio of density of ipsilateral/contralateral axons to the ischemia it is herein demonstrated that the UCBSCs of the present invention have the ability to induce sprouting of host nerve fibers in the brains of rats with ischemic brain injury (FIG. 8). These sprouting effects are unique observations that have not previously been described for other stem cells transplanted into the brain.

Example 7

Karyotyping of Umbilical Cord Blood Stem Cells

Figure 9:
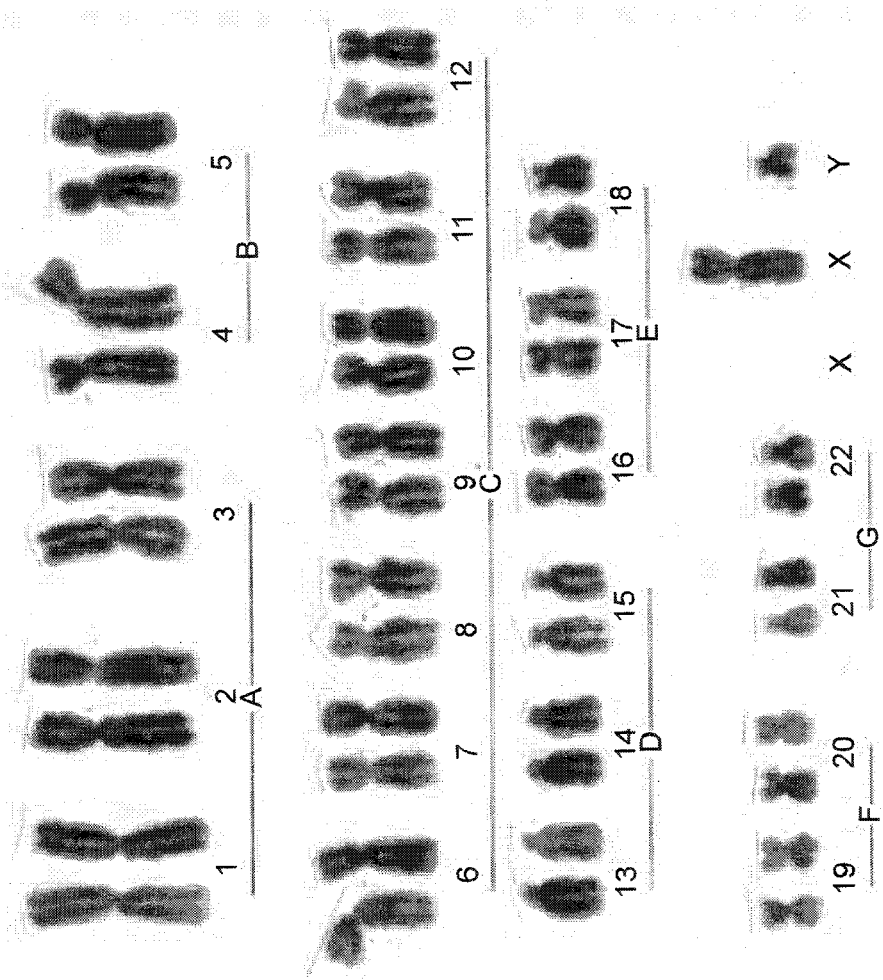
FIG. 9 depicts the karyotyping of human non-hematopoietic umbilical cord blood stem cells after 36 population doublings.

FIG. 9 demonstrates the karyotyping of the human non-hematopoietic umbilical cord blood stem cells that have been passaged for 36 population doublings. Note, there is a normal complement of human chromosomes without evidence of chromosomal abnormalities. This karyotyping suggests that the self-renewal observed by these cells is not due to the production of neoplastic cancer cells that arise from chromosomal truncations and translocations.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of treating damaged neuronal tissue in a human subject in need of such treatment comprising administering by intravenous or striatal delivery to the subject an effective amount of a composition comprising a population of human umbilical cord blood stem cells, or progeny cells thereof, that are Oct-4$^+$ and surface antigen negative for CD34, and that have been isolated, and cultured in culture medium containing serum, b-FGF (basic fibroblast growth factor) and EGF (epidermal growth factor), and a pharmaceutically acceptable carrier, wherein the neuronal tissue damage is due to ischemia; and wherein the treatment results in improved neurological performance compared to a control treated subject.

2. The method of claim 1, wherein the cells have the capacity to be induced to differentiate to form at least one differentiated cell type of neuronal origin.

3. The method of claim 1, wherein the tissue is brain or spinal cord tissue.

4. The method of claim 1, wherein the damage is due to stroke or to traumatic injury.

5. The method of claim 1, wherein the administration of the composition induces sprouting of subject nerve fibers.

6. The method of claim 1, wherein the size of cortical infarction following ischemic brain injury is reduced following the treatment as compared to a subject not treated with the composition following ischemic brain injury.

7. The method of claim 1, wherein the composition is administered into the body of the subject by localized injection.

8. The method of claim 1, wherein the composition is administered to the subject in conjunction with a suitable matrix implant.

9. The method of claim 8, wherein the matrix implant provides additional genetic material, cytokines, growth factors, or other factors to promote growth and differentiation of the cells.

10. The method of claim 1, wherein the cells are encapsulated prior to administration to the subject.

11. The method of claim 1, wherein the composition is administered intravenously.

12. The method of claim 1, wherein the composition is administered into the body of the subject by systemic injection.

13. The method of claim 1, wherein the cells are surface antigen negative for CD45 and HLA Class II.

14. The method of claim 1, wherein the cells are surface antigen positive for CD10, CD13, CD44, CD49, CD90 and HLA Class I.

15. The method of claim 1, wherein the cells are adherent mononuclear cells.

* * * * *

UNITED STATES PATENT AND TRADEMARK OFFICE
CERTIFICATE OF CORRECTION

PATENT NO.        : 8,309,070 B2
APPLICATION NO.   : 11/130820
DATED             : November 13, 2012
INVENTOR(S)       : Low et al.

Page 1 of 1

It is certified that error appears in the above-identified patent and that said Letters Patent is hereby corrected as shown below:

In Column 1, Line 5:

Replace:
This work was funded by United States Grant No. RO1-NS40831 from the National Institutes of Health. The government may have certain rights to this invention.

With:
This invention was made with government support under R01-NS40831 awarded by the National Institutes of Health. The government has certain rights in the invention.

Signed and Sealed this
Nineteenth Day of February, 2013

Teresa Stanek Rea
*Acting Director of the United States Patent and Trademark Office*